United States Patent
Clouet et al.

(10) Patent No.: US 11,484,596 B2
(45) Date of Patent: Nov. 1, 2022

(54) OPTIMIZED PROCESS FOR DIMERIC PEPTIDE-PHOSPHOLIPID CONJUGATE

(71) Applicant: Bracco Suisse SA, Cadempino (CH)

(72) Inventors: Anthony Clouet, Prevessin-Moens (FR); Bernard Lamy, Courmagnoux (FR)

(73) Assignee: Bracco Suisse SA, Cadempino (CH)

( * ) Notice: Subject to any disclaimer, the term of this patent is extended or adjusted under 35 U.S.C. 154(b) by 24 days.

(21) Appl. No.: 17/413,333

(22) PCT Filed: Dec. 16, 2019

(86) PCT No.: PCT/EP2019/085459
§ 371 (c)(1),
(2) Date: Jun. 11, 2021

(87) PCT Pub. No.: WO2020/127124
PCT Pub. Date: Jun. 25, 2020

(65) Prior Publication Data
US 2022/0202944 A1 Jun. 30, 2022

(30) Foreign Application Priority Data
Dec. 18, 2018 (EP) .................................... 18213539

(51) Int. Cl.
*A61K 47/54* (2017.01)
*C07K 1/18* (2006.01)

(52) U.S. Cl.
CPC .............. *A61K 47/544* (2017.08); *C07K 1/18* (2013.01)

(58) Field of Classification Search
None
See application file for complete search history.

(56) References Cited

U.S. PATENT DOCUMENTS

2005/0147555 A1    7/2005   Fan et al.

FOREIGN PATENT DOCUMENTS

WO    2007067979 A2    6/2007

OTHER PUBLICATIONS

Ferrara, N., "Vascular Endothelial Growth Factor: Basic Science and Clinical Progress," Endocrine Reviews, 25:581-611 (2004).
International Search Report and Written Opinion for PCT/EP2019/085459, dated Feb. 14, 2020.
Ramakrishnan, S. et al., "Vascular endothelial growth factor-toxin conjugate specifically inhibits KDR/flk-1-positive endothelial cell proliferation in vitro and angiogenesis in vivo," Cancer Research, 56:1324-1330 (1996).
Veikkola, T. et al., "Regulation of Angiogenesis via Vascular Endothelial Growth Factor Receptors," Cancer Res., 60:203-212 (2000).

*Primary Examiner* — Anand U Desai
(74) *Attorney, Agent, or Firm* — Vivicar Law, PLLC (57) ABSTRACT

The present invention discloses a new efficient process for the preparation of the KDR-targeting peptide-phospholipid conjugate of formula (I), which can be useful in therapeutic and diagnostic compositions and particularly in the preparation of ultrasound contrast agents.

16 Claims, 2 Drawing Sheets

OPTIMIZED PROCESS FOR DIMERIC PEPTIDE-PHOSPHOLIPID CONJUGATE

CROSS-REFERENCE TO RELATED APPLICATIONS

This application is the national stage application of corresponding international application number PCT/EP2019/085459, filed Dec. 16, 2019, which claims priority to and the benefit of European application no. 18213539.2, filed Dec. 18, 2018, which is hereby incorporated by reference in its entirety.

FIELD OF THE INVENTION

The present invention relates to the field of KDR-targeting peptide-phospholipid conjugates, which are useful in therapeutic and diagnostic compositions, and particularly to the methods of preparation of the same.

BACKGROUND OF THE INVENTION

Angiogenesis represents the formation of new blood vessels from pre-existing vasculature and plays a critical role not only in normal physiological processes but also in the pathogenesis of diseases such as cancer, rheumatoid arthritis and diabetic microvascular disease. For instance, angiogenesis is involved in the transition of a tumor from hyperplastic to neoplastic growth. Therefore, inhibition of the related pathological processes is very important in therapeutic and diagnostic cancer research.

When angiogenic growth factors are produced in excess of angiogenesis inhibitors, endothelial cells are stimulated to proliferate. Among the known and best characterized pro-angiogenic agents or growth factors, the vascular endothelial growth factors (VEGF) family, and in particular KDR (kinase insert domain receptor, also known as VEGFR-2 or Flk-1), represent those of greater interest as displaying more abundant endothelial cell expression and dominating the angiogenetic response[1]. The expression of KDR is highly upregulated in angiogenic vessels, especially in tumors, inducing a strong angiogenic response[2].

The VEGF binding activity of KDR in vivo is critical to angiogenesis, thus the ability to detect its upregulation on endothelial cells or to detect VEGF/KDR binding complexes would be extremely beneficial in detecting or monitoring angiogenesis.

It is known that for diagnostic and therapeutic purposes, such as for example for imaging vessels and internal organs, it would be particularly advantageous to incorporate into gas filled ultrasound contrast agents any targeting-vector composition which exhibits high binding affinity for the desired target, such as KDR. For example, KDR-targeting peptides-phospholipid conjugates can be used to prepare targeted gas filled ultrasound contrast agents.

It is well known in fact that gas filled ultrasound contrast agents are exceptionally efficient ultrasound reflectors for echography. For instance, injecting into the bloodstream of living bodies suspensions of gas filled microbubbles in a carrier liquid will strongly reinforce ultrasonic echography imaging, thus aiding in the visualization of internal anatomic structures, such as blood vessels.

One of the targeting vector compositions which exhibit high binding affinity for the target KDR, or the VEGF/KDR complex, is represented for example by the following compound (I), a conjugate "targeting peptide-phospholipid" (lipopeptide) that has been firstly described in patent application WO2007/067979 A2 and has exhibited high ability to bind to KDR-expressing tissues.

Figure 1:
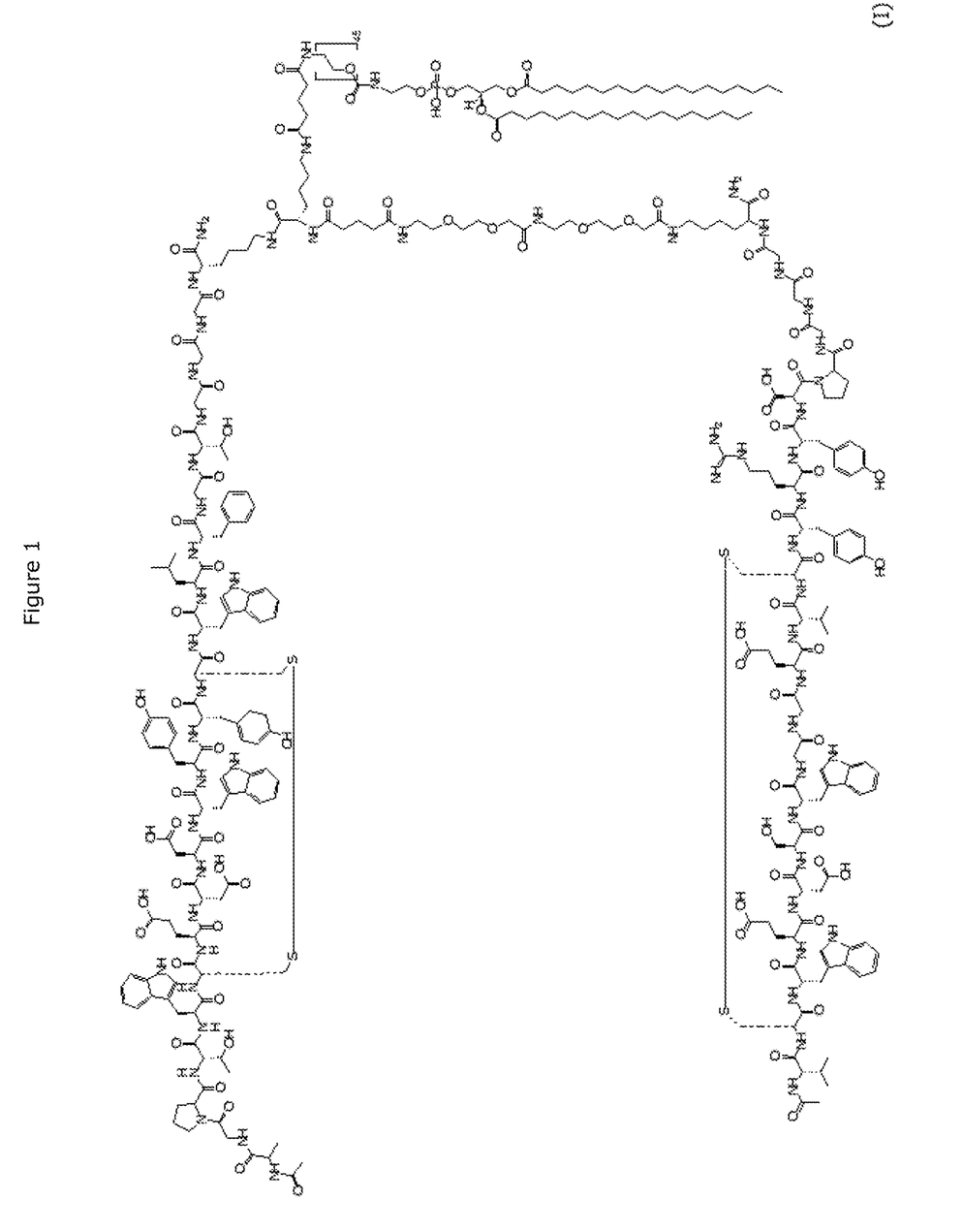
FIG. 1 shows the structure of the compound (I) prepared according to the invention.

Said compound (I), reported here below and in more detail in FIG. 1, is structurally constituted by a heterodimeric peptide formed by two different monomeric peptide chains, both of 23 amino acids, tethered by a glutaryl linker, and conjugated with a polyethyleneglycol moiety (PEG) such as $DSPE-PEG_{2000}-NH_2$ through a second glutaryl linker.

A method for the preparation of the KDR-binding peptide-phospholipid conjugate (I) has been described in WO2007/067979 A2 (see the therein reported Example 5, pages 52-54, and FIG. 4 for details).

The conjugate is prepared starting from automated solid phase synthesis of the peptide monomers, followed by their coupling and activation using succinimidyl glutarate (DSG), and subsequent conjugation of the obtained derivative with DSPE-PEG$_{2000}$-NH$_2$ via glutaryl linkage.

The last conjugation step is also illustrated in the following Scheme 1.

-continued (I)

It appears from the above disclosure, that the conjugation step could imply some drawbacks in terms of yield and purity of the final product (see par. [0063]: "any free phospholipid may complicate the purification and isolation of the final product"). In fact, the phospholipid reagent DSPE-PEG$_{2000}$-NH$_2$ (III), being difficult to be separated from the final product (I) through the known purification methods, is added in default with respect to the succinimidyl-dipeptide (II) (ratio between DSPE-PEG$_{2000}$-NH$_2$ and the succinimidyl-dipeptide: 0.9 to 1 equivalents) to prevent the formation of contaminants and the need of cumbersome purifications.

This approach, however, although limiting the impurities in the final product, causes a loss of the costly heterodimer (II) and affords yields of the conjugation step not higher than 60%, or even not higher than 30%. Moreover, the final compound after preparative HPLC purification, as disclosed in Example 5 of WO2007/067979, still retains almost 2% of impurities, with a purity profile which is not in compliance with the requirements set up by the authorities for a pharmaceutical product.

Another drawback of the known process is linked to the presence of high contents of trifluoroacetic acid (TFA), which is added during the synthesis for solubilisation and in the mobile phases for the preparative HPLC purification. In fact, besides the fact that TFA is considered to be a pharmaceutically unacceptable salt, when the product is stored as TFA salt in form of lyophilizate at 5° C. or in solution, it has been observed a degradation likely formed by TFA-promoted acid hydrolysis of one of the phospholipid fatty acid esters in the dimer conjugate to provide a lyso-compound as undesired impurity, as described in par. [0065]-[0066] of WO2007/067979. Thus, further onerous and time-consuming procedures have to be carried to "convert the TFA salts of the dimer peptide-phospholipid conjugate" in another more stable salt.

In short, the main problems of the known process are represented by a detrimental loss of the expensive heterodimer (II) during the conjugation step with the pegylated phospholipid (III); the difficult purification step compromising the purity and yield of the final product; and the instability of the final product obtained and stored as TFA salt.

Therefore the disclosed approach, although quite effective, can be very burdensome and does not yet represent a valid and industrially applicable method. Purity and production efficiency parameters are not to be met yet.

Conversely, in order to use such targeting peptide-phospholipid conjugate in vivo in imaging of vessels and internal organs, it would be particularly beneficial to have an efficient method for large-scale production of highly purified forms of the product.

SUMMARY OF THE INVENTION

The present invention provides a new process for the preparation of the peptide-phospholipid compound (I) as defined above, characterized by optimized conditions of the conjugation and purification steps. This process results particularly useful for the manufacturing of gas filled ultrasound contrast agents.

In this context, it has been found an efficient analytical procedure remarkably improving the separation of the final compound from the by-products, thereby allowing to increase the amount of starting material (III) during the conjugation and to obtain the compound (I) in higher yields, with best purity profile and a suitable stability profile, useful for the scalability of the whole process.

Accordingly, it is a first aspect of the present invention a process for the preparation of compound (I), or pharmaceutically acceptable salts thereof,

(I)

comprising the step of
(i) coupling the corresponding succinimidyl ester intermediate (II)

(II)

with the DSPE-PEG$_{2000}$-NH$_2$ phospholipid with the DSPE-PEG$_{2000}$NH$_2$ phospholipid (III)

in the presence of DIEA,
wherein said phospholipid (III) is present in excess with respect to compound (II).

In a preferred embodiment, the coupling is carried out with 1.1 or more equivalents of phospholipid (III) per equivalent of compound (II).

In a more preferred embodiment, the coupling is carried out with two equivalents of phospholipid (III) per equivalent of compound (II).

In another aspect, the present invention provides said process further comprising the steps of:
(ii) isolating the crude product (I) recovered from the reaction mixture of step (i);
(iii) optionally diluting in water the crude product obtained in step (ii) and adding a base to reach a pH comprised between 6 and 8; and
(iv) purifying the crude product from the solution of step (iii).

The addition of a base in step (iii) can facilitate the complete solubilization of the crude product in water, keeping the pH of the solution between 6 and 8. Preferably, a suitable amount of 0.1 N NaOH is added to reach a pH between 6.5 and 7.5, more preferably to reach pH 7.3.

According to the invention, the purification of step (iv) can be carried out by reverse phase high performance liquid chromatography (RP-HPLC) or by ion exchange chromatography or by both RP-HPLC and ion exchange chromatography.

In a preferred embodiment, the purification is carried out by RP-HPLC purification only. According to the invention, the chromatographic separation by RP-HPLC is achieved preferably using eluents having pH comprised between 6 and 8 and comprising a volatile salt easy to be removed. An optimal mobile phase can be represented for instance by the combination of eluent A, consisting of 10 mM AcONH$_4$ in water, and eluent B, consisting of 10 mM AcONH$_4$ in water/acetonitrile 1/9.

In another preferred embodiment, the purification is carried out by ion exchange chromatography. Preferably, such chromatography is performed with an anion exchange resin (e.g. ANX Sepharose resin) and a buffer solution selected from those commonly used for ion chromatography at pH preferably between 7 and 8, optionally with the addition of water miscible solvents improving the solubilization of a phospholipid moiety.

According to a preferred embodiment of the invention, the purification is successfully carried out by using a Tris.HCl/NaCl buffer as eluent. A suitable chromatographic separation is obtained for instance by using 0.05 M Tris.HCl+0.10 M NaCl (pH 7.5)+35% iPrOH as fixation buffer and 0.05 M Tris.HCl+1.00 M NaCl (pH 7.5)+35% iPrOH as elution buffer.

In a further aspect of the invention, it is provided the above process, wherein compound (II) is prepared by activation of the terminal alkyl-amino moiety of the corresponding intermediate of formula (IV) with di(N-succinimidyl) glutarate (V), as reported in the following Scheme 2 (step i')).

Scheme 2

The process of the invention is thus characterized by the use of an excess of the phospholipidic reagent DSPE-PEG$_{2000}$-NH$_2$ (III), which reacts with all the present amount of the activated heterodimer (II), such as to avoid any loss of the latter expensive intermediate. The yields of the coupling steps (i') and in particular (i) are now advantageously higher compared to those obtained with the previously known procedure.

In fact, the previous method only provides yields lower than 60% of the dimer peptide phospholipid conjugate, which needs to be converted from TFA salt to a more stable salt, thus further lowering the effective recovery of the final product.

Conversely, the present method allows obtaining compound (I) with improved yields of at least 69% and most importantly, it provides for more efficient methods of analytical separation and preparative purification of the final product from the undesired impurities and removal of the excess reagents; thus, the optimized purification conditions allow to obtain the final product with a purity higher than 99% after RP-HPLC.

Therefore, according to the several benefits provided by the present process, the new procedure for the synthesis of compound (I) solve the drawbacks of the previously disclosed procedure and can be particularly suitable for scaling-up and industrial production.

DESCRIPTION OF THE INVENTION

DEFINITIONS

In the present description, and unless otherwise provided, the following terms are intended to have the following meanings.

The term "heterodimer" refers to a molecule composed of two polypeptide chains differing in composition, i.e. in the order, number, or kind of their amino acid residues. In particular, it is herein mentioned with reference to the compound of formula (I) or its precursors (II) and (IV), as above defined.

The term "pegylated" refers to a molecule that is covalently attached to a polyethylene glycol (PEG) polymer chain. The pegylated compound can be achieved by incubation of a reactive derivative of PEG, preferably after functionalization at one or both terminals with a reactive moiety, with the target molecule.

The term "anion exchange solid phase" means solid support able to perform an exchange of anions with the solution or suspension in contact thereto. Said contact may be obtained by elution through a column packed with the proper solid phase.

Detailed Description of the Embodiments

The method herein described relates to the preparation of the compound of formula (I), as defined above, and has the advantages to save amounts of the expensive starting material while providing the final product in high yields and with an optimal purity degree.

These results can be accomplished, among others, by the finding of two efficient purification methods, which can be applied separately or in combination, allowing effective removal of the unreacted phospholipid (III) added in excess in the coupling step (i), together with any other undesired by-product.

The preparation of the compound (I), according to the synthetic approach described in WO2007/067979, provides for an activation of the heterodimer (IV) as above defined, prepared for instance by known solid phase synthesis methods, with a di(N-succinimidyl)glutarate (V) and subsequent conjugation of the activated heterodimer (II) with DSPE-PEG$_{2000}$-NH$_2$ (III). The latter step, as said above, is carried out in defect of the phospholipid, thus the coupling is only accomplished with poor yield results.

Conversely, the optimized process represented by the present invention provides for remarkable improvement of the conjugation step, as described below in detail.

The heterodimer (IV) can be activated for instance by following the same procedure reported in example 5 of WO2007/067979 (paragraph [00124]), i.e. by reacting the heterodimer precursor with an excess of di(N-succinimidyl) glutarate and a base, such as DIEA, for instance with 5-fold excess of both reactants to avoid the heterodimer condensation. After completion of the reaction, the mixture can be diluted with a suitable solvent, such as anhydrous ethyl acetate, in order to precipitate the heterodimer glutaric acid monoamide mono-NHS ester (II) which is then recovered and washed to remove the remaining traces of reactants. Alternatively, the mixture can be concentrated to remove the solvent and the dry crude can be washed, for instance with EtOAc, and centrifuged, recovering the solid from the flask.

Coupling with the Phospholipid

According to the invention, and as described in more detail in the experimental part, the compound of formula (II) is incubated with an excess amount of DSPE-PEG$_{2000}$-NH$_2$ (III) dissolved in DMF and in the presence of a base, such as DIEA. The ratio between the equivalents of heterodimer precursor (II) and the equivalents of phospholipid (III) is at least 1:1.1, but more conveniently is comprised between 1:1.1 and 1:5. Preferably, it is 1:2.

The completeness of the coupling reaction can be monitored by analytical HPLC.

Isolation of the Product

The crude product can be collected after the concentration of the reaction mixture. For instance, part of the excess reagents can be removed by means of washings of the dry crude with a suitable solvent and centrifugation of the mixture. Alternatively, a solvent, such as ethyl acetate, can be added to promote precipitation of the final product, which can be then isolated by filtration and dried.

Preferably, the mixture is purified by chromatography, as described below. Before the chromatography step, the reaction mixture can be concentrated under reduced pressure for recovering the crude product, which is then dissolved in an aqueous medium such as water, optionally by addition of a base, such as for instance NH$_4$OH 0.1N, to promote the complete solubilization at a pH comprised between 6 and 8, preferably at pH of about 7.3; the limpid solution is preferably filtrated on a 0.2 µm filter.

Chromatographic Purification

According to the invention, the crude product is purified by RP-HPLC, by ion exchange chromatography or by both techniques.

Typically, the separation by RP-HPLC is preferred as it is more efficient in separating the pure product from the excess reagents. However, in cases when residual traces of phospholipid (III) remain in the final product (typically more than 1%) a fast and reliable ion exchange purification step can also be added or carried out in alternative. The preparative HPLC purification according to the invention is preferably performed on a reverse phase C4 preparative column, eluted with a mobile phase comprising AcONH$_4$ salt. In one embodiment the mobile phases are represented by aqueous solutions of 10 mM AcONH$_4$ and 10 mM AcONH$_4$/acetonitrile 1/9, mixed in a gradient composition able to well separate the product from the phospholipid.

The ion exchange purification according to the invention is conveniently performed on an anion exchange resin, preferably on a weak anion exchanger resin with tertiary amine groups attached to the base matrix. The separation of the final product from the excess reagents and other impurities is carried out by selection of the suitable buffers for the fixation and elution phase. According to the invention, optimal results were obtained by using a Tris.HCl/NaCl buffer solution at different concentrations of salt and at pH comprised from about 7 to about 8, with the addition of a percentage of a solvent, such as for instance iPrOH.

The modulation of the salt concentration in the buffer allows to fix the product to the solid phase while eluting all the by-products, and subsequently to elute and collect the pure product.

This useful method for removing all the traces of the phospholipid (III) makes possible to use this reagent even in large excess during the conjugation reaction with the heterodimer (II).

Therefore, as widely described above, the present invention allows for a more convenient and reliable process for the preparation of compound (I), with high yields and degree of purity, which can be also applied on an industrial scale.

In fact, the product obtained with the present process is substantially free of by-products and in line with the purity specifications required for its use in the manufacturing of gas filled ultrasound contrast agents.

The present invention will be now illustrated with examples that are not intended to pose any limitation to its scope.

Experimental Part

Materials and Equipment

Solvents such as DMF and ethyl acetate were always used neat and dried to minimize exposure time to ambient air.

The heterodimer acetate (IV) was provided by Bachem (Bubendorf, Switzerland). DSPE-PEG$_{2000}$-NH$_2$ ammonium salt was purchased from Avanti Polar Lipids Inc. (USA).

Analytical reversed phase HPLC was performed on a SHIMADZU UFLC system consisting of a UFLC binary solvent manager, a UFLC controller (CBM-20A) and a HPLC UV-VIS detector (SPD-20A). Analyses were performed using a linear gradient of phase A (10 mM AcONH$_4$ in H$_2$O) and phase B (10 mM AcONH$_4$ in ACN/H$_2$O 9/1) at 1.5 mL/min with UV detection at 214 nm. 40 µL were injected and the column temperature was 25° C.

Preparative RP-HPLC was performed on a Shimadzu preparative system consisting of HPLC binary solvent manager, HPLC fraction collector (FRC-10A), HPLC controller (SCL-10A) and HPLC UV/VIS detector (SPD-10AV). The system was equipped with a Kromasil C4 300 Å (10×250 mm) column. Purification was performed by eluting with a linear gradient of phase A (10 mM AcONH$_4$ in H$_2$O) and phase B (10 mM AcONH$_4$ in ACN/H$_2$O 9/1) at 5 mL/min with UV detection at 214 nm. 3 mL was injected and column temperature was 25° C.

The purity of the final product has been analyzed by an Acquity™ Ultra Performance LC System (Waters) equipped with TUV detector and a Acquity BEH Phenyl 1.7 µm (2.1×150 mm) column or by an Agilent 1100 LC System equipped with UV and Evaporative Light Scattering Detector (ELSD Sedex 85) and a Zorbax 300SB 3.5 µm (3×150 mm) column.

The abbreviations for individual amino acid residues are conventional: for example, Asp or D is aspartic acid, Gly or G is glycine, Arg or R is arginine. The amino acids herein referred to should be understood to be of the L-isomer configuration unless otherwise noted.

| List of abbreviations | |
|---|---|
| AA, aa | Amino acid |
| ACN | Acetonitrile |

| List of abbreviations | |
|---|---|
| AcOEt | Ethyl acetate |
| Adoa | 8-amino-3,6-dioxaoctanoic acid |
| DIEA | N,N-Diisopropylethylamine |
| DMF | Dimethylformamide |
| DSG | Di(N-succinimidyl)glutarate |
| DSPE-PEG$_{2000}$-NH$_2$ | 1,2-Distearoyl-sn-glycero-3-phosphoethanolamine-N-[amino(polyethylene glycol)-2000] |
| ELSD | Evaporative light scattering detector |
| Eq. | Equivalent |
| Fmoc | 9-Fluorenylmethoxycarbonyl |
| g | Gravitational acceleration |
| H$_2$O | Water |
| HPLC | High performance liquid chromatography |
| iPrOH | Isopropyl alcohol |
| mg | Milligram(s) |
| Min | Minute(s) |
| mL | Milliliter(s) |
| mM | Millimolar |
| Rt | Retention time |
| TFA | Trifluoroacetic acid |
| THF | Tetrahydrofuran |
| TUV | Tunable ultra violet |
| UV | Ultra violet |
| Vol. | Volume |
| UPLC | Ultra performance liquid chromatography |

Example 1: Preparation of the Intermediate (II)

Before conjugation with the pegylated phospholipid, the heterodimer (IV) has been activated by coupling with a di(N-succinimidyl)glutarate moiety as a linking agent. A solution of heterodimer acetate (49.08 mg) in 500 µL DMF was added portionwise (7×70 µL) every 2 minutes to a disuccinimidylglutarate solution with DIEA (130 µL). To avoid dimer condensation, an excess of DSG (5 eq.) and DIEA (5 eq.) was used. After stirring at room temperature for 30 min after the last addition, the activated heterodimer was isolated and analysed by HPLC to confirm the reaction completeness. For these analyses, the following chromatographic conditions were applied:

Column: Phenomenex Luna 5µ C18 (250×4.6 mm)

Eluent A: 10 mM AcONH$_4$ in H$_2$O

Eluent B: 10 mM AcONH$_4$ in H$_2$O/ACN (1/9)

Flow rate: 1.5 mL/min

Detector: UV 214 nm

Gradient: from 25% to 52% of mobile phase A

Retention time: 12.69 min

Example 2: Isolation of Compound (II)

Compound (II) obtained in example 1 was isolated to remove the excess of DSG from the reaction mixture. The suspension was concentrated under reduced pressure to remove DMF. The dry crude was washed with 10 mL EtOAc and then centrifuged 3 min at 2500 g. The supernatant was decanted in a 100 mL round bottom flask while solid was washed twice with 15 mL of EtOAc and dried under reduced pressure yielding 47.02 mg of a white powder.

Example 3: Synthesis of Compound (I)

The synthesis of compound (I) was performed according to the step reported in Scheme 1. The reaction progress was followed using analytical reversed phase HPLC or UPLC with UV detector at 220 nm or ELSD detector.

Steps i)-iii) Conjugation and Isolation of the Product (I)

A sample of DSPE-PEG$_{2000}$-NH$_2$ ammonium salt (18 μmol, 50.23 mg, 2 eq.) was dissolved in 300 μL of anhydrous DMF and then DIEA was added (2 eq.) to reach a total volume of 315 μL.

Compound (II) was solubilised in 400 μL of DMF, then added in five portions to the mixture of DSPE-PEG$_{2000}$-NH$_2$ and DIEA and let overnight under stirring.

An aliquot was collected for analytical HPLC monitoring and the profile showed a main peak eluting at a retention time of about 12.5 min. The mixture was then concentrated under reduced pressure recovering 105.5 mg of crude product. 5 mL of water was firstly added reaching a pH of 4.8; however, to obtain a complete solubilisation and a limpid solution, about 20 drops of 0.1 N NH$_4$OH were further added reaching pH 7.3. Then, the solution was filtrated on 0.2 μm and rinsed to obtain a final volume close to 9 mL ready for preparative HPLC purification.

Example 4: Purification of Compound (I) by RP-HPLC

Preparative HPLC purification of the final crude product (I) has been performed with the same stationary phase as for the analytical monitoring of the coupling reaction. Therefore, a Kromasil 10μ 300 Å C4 column (250×10 mm) was equilibrated with 10 mM AcONH$_4$ in a mixture water:acetonitrile (1:9) before loading the sample divided in 3 aliquots (3×3 mL). In detail, the liquid phases and elution conditions applied for purification are reported below:

Column: Kromasil 10μ 300 Å C4 (250×10 mm)
Eluent A: 10 mM AcONH$_4$ in H$_2$O
Eluent B: 10 mM AcONH$_4$ in H$_2$O/ACN (1/9)
Flow rate: 5 mL/min
Injection vol.: 3.0 mL
Column temperature: 25° C.
Detector: UV 214 nm
Gradient:

| Time (min) | Eluent A % | Eluent B % |
|---|---|---|
| 0 | 100 | 0 |
| 5 | 100 | 0 |
| 45 | 0 | 100 |
| 55 | 0 | 100 |
| 60 | 100 | 0 |
| 65 | 100 | 0 |

The collection was performed in 10 mL fractions leading to 30 mL of purified product for each run. Then, the 90 mL obtained from the 3 runs was concentrated under reduced pressure removing most of the acetonitrile before lyophilisation. The final product was recovered as a white solid (51.6 mg) with a yield of 69% from the starting heterodimer (IV).

Figure 2:
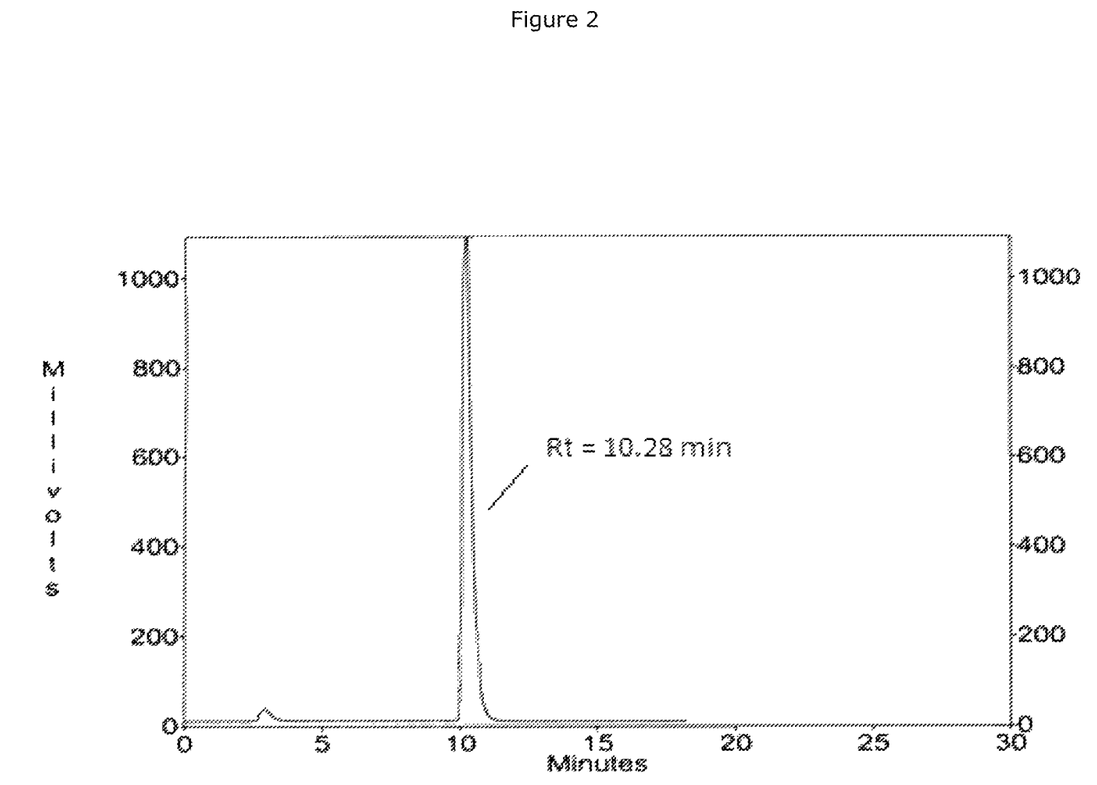
FIG. 2 shows a UPLC-ELSD chromatogram of compound (I) after the final HPLC purification.

Analysis of the purified product (I) performed with UPLC-UV method confirmed purity of 99%. No trace of DSPE-PEG$_{2000}$-NH$_2$ was detected (see FIG. 2).

Example 5: Purification of Compound (I) by Ion Exchange Chromatography

An ion exchange chromatography method has been optimized in order to further purify the crude product (I) in case of presence of traces of DSPE-PEG$_{2000}$-NH$_2$.

To this purpose a column packed with ANX Sepharose 4 fast flow resin (GE Healthcare) was used with the following buffers:

for fixation step: 0.05 M Tris.HCl-0.10 M NaCl-pH 7.5+35% iPrOH
for elution step: 0.05 M Tris.HCl-1.00 M NaCl-pH 7.5+35% iPrOH
for desalting step: 0.02 M Tris.HCl pH 7.5

Two samples of compound (I) (solutions A and B, respectively containing 0.5 mg and 1.5 mg of compound (I)) were loaded on an ANX column. Separately, the same experiment was performed with DSPE-PEG$_{2000}$-NH$_2$ (solutions C and D, respectively containing 0.5 mg and 1.5 mg of DSPE-PEG$_{2000}$-NH$_2$).

Fractions analysis revealed that DSPE-PEG$_{2000}$-NH$_2$ was eluting entirely with the first two column volumes (CV) with the fixation buffer. On the other hand compound (I) was not detected within the first two fractions, meaning that the separation could be effective as one is passing directly through when the other compound remains fixed to the resin.

Indeed, after passing 4 CV of fixation buffer in total, elution buffer was introduced allowing compound (I) to be collected in fractions within two CV (see Table 1a, solution A and B). Again, with the second experiment, it was confirmed that no DSPE-PEG$_{2000}$-NH$_2$ elutes after the second fraction even with elution buffer (Table 1b, solution C and D).

The pool of collected fractions was passed through a desalt Sephadex G-25M column before lyophilisation.

TABLE 1A

| Retention and elution of compound (I) (solutions A and B) on ANX column | | |
|---|---|---|
| Column volumes | mg compound (I) | recovery |
| Solution A (0.5 mg) | | |
| CV1 (fixation) | <0.010 | <2% |
| CV2 (fixation) | 0 | 0% |
| CV3 + 4 (fixation) | 0 | 0% |
| CV1 (elution) | 0.415 | 90% |
| CV2 (elution) | 0.050 | 11% |
| CV3 (elution) | 0 | 0% |
| Solution B (1.5 mg) | | |
| CV1 (fixation) | 0 | 0% |
| CV2 (fixation) | 0 | 0% |
| CV3 + 4 (fixation) | 0 | 0% |
| CV1 (elution) | 1.659 | 108% |
| CV2 (elution) | 0.014 | 1% |
| CV3 (elution) | 0 | 0% |

TABLE 1B

| Retention and elution of DSPE$_{2000}$-NH$_2$ (solutions C and D) on ANX column | | |
|---|---|---|
| Column volumes | mg DSPE$_{2000}$-NH$_2$ | recovery |
| Solution C (0.5 mg) | | |
| CV1 (fixation) | 0.477 | 95.4% |
| CV2 (fixation) | 0.004 | 0.7% |
| CV3 + 4 (fixation) | 0 | 0% |
| CV1 (elution) | 0 | 0% |
| CV2 (elution) | 0 | 0% |
| CV3 (elution) | 0 | 0% |
| Solution D (1.5 mg) | | |
| CV1 (fixation) | 1.403 | 93.5% |
| CV2 (fixation) | 0.014 | 0.9% |

TABLE 1B-continued

Retention and elution of DSPE$_{2000}$-NH$_2$
(solutions C and D) on ANX column

| Column volumes | mg DSPE$_{2000}$-NH$_2$ | recovery |
|---|---|---|
| CV3 + 4 (fixation) | 0 | 0% |
| CV1 (elution) | 0 | 0% |
| CV2 (elution) | 0 | 0% |
| CV3 (elution) | 0 | 0% |

All fractions were analysed through a 1100 LC/MSD system (Agilent) and quantified from a calibration standard using a UV detector, for compound (I), or an ELSD detector, for DSPE-PEG$_{2000}$-NH$_2$ (III).

REFERENCES

1. Ferrara N. et al., "Vascular Endothelial Growth Factor: Basic Science and Clinical Progress", *Endocrine Reviews*, 2004, 25(4), 581-611;
2. Veikkola T. et al., "Regulation of Angiogenesis via Vascular Endothelial Growth Factor Receptors", *Cancer Res.*, 2000, 60, 203-212.

The invention claimed is:

1. A process for the preparation of compound (I), or pharmaceutically acceptable salts thereof, comprising the step of
(i) coupling the corresponding succinimidyl ester intermediate (II)

-continued with the DSPE-PEG$_{2000}$-NH$_2$ phospholipid (III)

in the presence of DIEA,
wherein said phospholipid (III) is present in excess with respect to compound (II).

2. The process according to claim 1 wherein the coupling is carried out with 1.1 or more equivalents of phospholipid (III) per equivalent of compound (II).

3. The process according to claim 1 or 2 wherein the coupling is carried out with 2 equivalents of phospholipid (III) per equivalent of compound (II).

4. The process according to claim 1, further comprising the steps of
 (ii) isolating the crude product (I) recovered from the reaction mixture of step (i);
 (iii) optionally diluting in water the crude product obtained in step (ii) and adding a base to reach a pH comprised between 6 and 8; and
 (iv) purifying the crude product from the solution of step (iii).

5. The process according to claim 4, wherein the solution of step (iii) is brought to a pH between 7.0 and 7.5.

6. The process according to claim 4, wherein the purification of step (iv) is carried out by reverse phase high performance liquid chromatography (RP-HPLC).

7. The process according to claim 4, wherein the purification of step (iv) is carried out by ion exchange chromatography.

8. The process according to claim 4, wherein the purification of step (iv) is carried out by both a reverse phase high performance liquid chromatography (RP-HPLC) and an ion exchange chromatography.

9. The process according to claim 6 or 8, wherein the RP-HPLC purification is performed with a mobile phase comprising AcONH$_4$ salt.

10. The process according to claim 7 or 8, wherein the ion exchange chromatography is performed with a weak anion exchanger resin and a buffer solution at pH between 7 and 8.

11. The process according to claim 10, wherein the elution solution is the buffer 0.05 M Tris.HCl+1.00 M NaCl+35% iPrOH.

12. The process according to claim 1, wherein compound (II) is prepared by activation with di(N-succinimidyl)glutarate of the corresponding intermediate of formula (IV)

13. The process according to claim 2, wherein the coupling is carried out with 2 equivalents of phospholipid (III) per equivalent of compound (II).

14. The process according to claim 8, wherein the RP-HPLC purification is performed with a mobile phase comprising $AcONH_4$ salt.

15. The process according to claim 8, wherein the ion exchange chromatography is performed with a weak anion exchanger resin and a buffer solution at pH between 7 and 8.

16. The process according to claim 15, wherein the elution solution is the buffer 0.05 M Tris·HCl+1.00 M NaCl+35% iPrOH.

* * * * *